United States Patent
Zhao

(10) Patent No.: US 6,448,010 B1
(45) Date of Patent: Sep. 10, 2002

(54) METHOD FOR DETECTING MUTATIONS USING ARRAYED PRIMER EXTENSION

(75) Inventor: Xiaodong Zhao, Bridgewater, NJ (US)

(73) Assignee: Amersham Pharmacia Biotech, Inc., Piscataway, NJ (US)

( * ) Notice: Subject to any disclaimer, the term of this patent is extended or adjusted under 35 U.S.C. 154(b) by 0 days.

(21) Appl. No.: 09/678,981

(22) Filed: Oct. 4, 2000

Related U.S. Application Data

(60) Provisional application No. 60/157,937, filed on Oct. 6, 1999, now abandoned.

(51) Int. Cl.$^7$ .............................. C12Q 1/68; C12P 19/34

(52) U.S. Cl. ........................... 435/6; 435/91.1; 435/91.2

(58) Field of Search ........................... 435/6, 91.1, 91.2

(56) References Cited

U.S. PATENT DOCUMENTS

| | | | |
|---|---|---|---|
| 5,679,524 A | * | 10/1997 | Nikiforov et al. ............. 435/6 |
| 5,710,028 A | * | 1/1998 | Eyal et al. .................. 435/91.1 |
| 5,837,860 A | * | 11/1998 | Anderson et al. .......... 536/25.3 |

FOREIGN PATENT DOCUMENTS

| | | |
|---|---|---|
| WO | WO97/35033 | 9/1997 |
| WO | WO98/28438 | 7/1998 |
| WO | WO98/44152 | 10/1998 |
| WO | WO99/27137 | 6/1999 |
| WO | WO99/39001 | 8/1999 |

OTHER PUBLICATIONS

Stratagene 1988 Catalog, p. 39, 1988.*
Metspalu, A. "Arrayed Primer Extension as a Tool for DNA Diagnostics", Clinical Chemistry and Laboratory Medicine, Walter De Gruyter Und Co, DE, vol. 37, No. SUPPL, 1999, p. S46, XP000890197.
Gerhold, D., et al. "DNA chips: promising toys have become powerful tools", Tibs Trends in Biochemical Sciences, Elsevier Publication, Cambridge, EN, vol. 24, No. 5, May 1, 1999, pp. 168–173, XP004167912.
WO95/00669, Jan. 5, 1995, WIPO.

* cited by examiner

Primary Examiner—Jezia Riley
(74) Attorney, Agent, or Firm—Royal N. Ronning, Jr.; Stephen G. Ryan

(57) ABSTRACT

A method for detecting a mutation in a target nucleic acid sequence that comprises attaching oligonucleotide primers to a substrate, wherein the oligonucleotide primers have a sequence that is complementary to the target nucleic acid sequence, and wherein the oligonucleotide primers are grouped according to the identity of the first base which would be expected to be added to the primer through the process of primer extension; hybridizing to the oligonucleotide primers a sample nucleic acid sequence which possibly contains a mutation; extending each oligonucleotide primer by one base using a reaction mixture comprising labeled ddNTPs; and detecting a mutation in the sample nucleic acid sequence by detecting the presence of a labeled ddNTP which does not correspond to the identity of the base expected to be added to the primer through the process of primer extension. Mutations may be detected in mRNA or DNA. The labeled ddNTPs may be labeled with a fluorescent dye, a chemiluminescent reagent, a radioactive label. or an electrically conductive tag. A nucleic acid array and a kit for detecting genetic mutations are also disclosed.

12 Claims, 8 Drawing Sheets

ATTACHMENT

SLIDE

SEQUENCE LISTING

<160> NUMBER OF SEQ ID NOS: 4

<210> SEQ ID NO 1
<211> LENGTH: 28
<212> TYPE: DNA

```
<213> ORGANISM: Artificial Sequence
<220> FEATURE:
<223> OTHER INFORMATION: Description of Artificial Sequence: synthetic
      oligonucleotide

<400> SEQUENCE: 1
aaatggcccc tcctcagcat cttatccg                                          28

<210> SEQ ID NO 2
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 2
aaatcactga ttgctcttag gtctggcc                                          28

<210> SEQ ID NO 3
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 3
aaattcctca ctgattgctc ttaggtct                                          28

<210> SEQ ID NO 4
<211> LENGTH: 28
<212> TYPE: DNA
<213> ORGANISM: Artificial Sequence
<220> FEATURE:
<223> OTHER INFORMATION: Description of Artificial Sequence: synthetic
      oligonucleotide

<400> SEQUENCE: 4
aaaactgatt gctcttaggt ctggcccc                                          28
```

METHOD FOR DETECTING MUTATIONS USING ARRAYED PRIMER EXTENSION

This Application claims the benefit of priority under 35 U.S.C. §119(e) based on U.S. provisional application No. 60/157,937, filed Oct. 6, 1999, which is now abandoned.

BACKGROUND OF THE INVENTION

Upon completion of the human genome project, genotyping of individuals will become possible and important to trace biological reactions of each individual. This is one of the conceptions for health care in the future. Molecular medicine is expected to evolve for each individual based on his or her genetic identity. Chip-based nucleic acid sequence analysis is a powerful tool for re-sequencing gene to identify single nucleotide polymorphisms (SNP), which is believed to be responsible for individual identity. Spacially addressed primer array offers a cheap and effective method for SNP detection. However, to justify the signal of each spot in the entire array and to analyze the complete data is very tedious and requires decent software. Herein, I describe a novel format of arrayed primer extension, which simplifies the data analysis and leads to straightforward answer.

The current art of spotting microarray on a chip has the oligonucleotides laid on a chip sequentially from one end (3' or 5') to the other end (5' or 3') of the target. As shown in FIG. 1, the primers add one base difference as they proceed from one end to the other end. A complete hybridization map to the arrayed primers reveals the sequence of the gene in question.

FIG. 2 shows a fluorescent image of a conventional oligonucleotide array which has been hybridized with a sample nucleic acid and subjected to a primer extension reaction. The four terminators are labeled with four fluorescent dyes. Each terminator that has been incorporated onto the oligonucleotide primer may be identified on the image by color. The image of the dye terminator labeled spots was obtained using an Avalanche microscanner (Molecular Dynamics, Sunnyvale, Calif.). As depicted in FIG. 2, it is difficult to ascertain the presence of mutations in samples using such sequentially placed oligonucleotide primer arrays without the aid of complex software.

While nucleotide arrays present many advantages in the analysis of nucleic acid sequences, improvements in the techniques incorporating such arrays are still possible.

BRIEF SUMMARY OF THE INVENTION

A method for detecting a mutation in a target nucleic acid sequence that comprises: attaching oligonucleotide primers to a substrate, wherein the oligonucleotide primers have a sequence that is complementary to the target nucleic acid sequence, and wherein the oligonucleotide primers are grouped according to the identity of the first base which would be expected to be added to the primer through the process of primer extension; hybridizing to the oligonucleotide primers a sample nucleic acid sequence which possibly contains a mutation; extending each oligonucleotide primer by one base using a reaction mixture comprising labeled ddNTPs and enzyme; and detecting a mutation in the sample nucleic acid sequence by detecting the presence of a labeled ddNTP which does not correspond to the identity of the base expected to be added to the primer through the process of primer extension. The sample nucleic acid sequence may be mRNA or DNA. The labeled ddNTPs may be labeled with a fluorescent dye, a chemiluminescent reagent, a radioactive label, a redox tag, or an electrically conductive tag.

The instant invention also pertains to a nucleic acid array comprising a substrate containing oligonucleotide primers having a sequence complementary to a target nucleic acid sequence, wherein the oligonucleotide primers are grouped according to the identity of the first base which would be expected to be added to the primer through the process of primer extension after hybridizing with a sample nucleic acid sequence.

The instant invention also pertains to a kit for detecting genetic mutations comprising the nucleic acid array as described above.

The instant invention also pertains to a method for detecting a mutation in a target nucleic acid sequence that comprises: identifying the base expected to be added to a primer located at a particular coordinate on an oligonucleotide array as expected from the target nucleic acid sequence; identifying the base actually added to the primer located at the particular coordinate on the oligonucleotide array through the process of primer extension; comparing the base actually added to the primer at the particular coordinate with the base expected to be added to the primer at the particular coordinate; and reporting those instances where the bases are not the same, in order to identify a mutation.

BRIEF DESCRIPTION OF THE DRAWINGS

The file of this patent contains at least one drawing executed in color. Copies of this patent with color drawing(s) will be provided by the Patent and Trademark Office upon request and payment of the necessary fee.

DETAILED DESCRIPTION OF THE INVENTION

Figure 3:
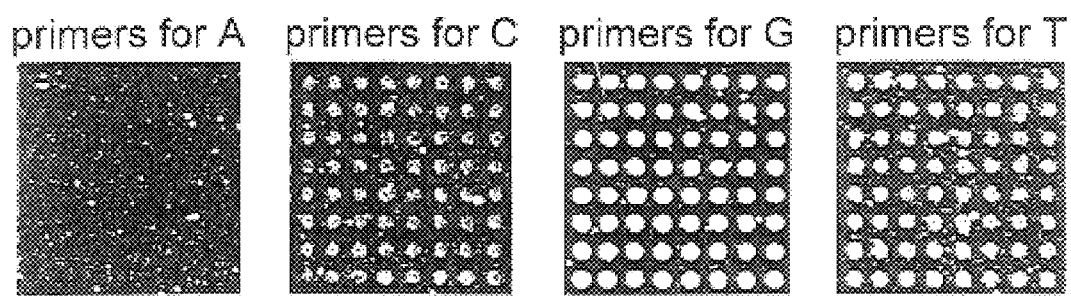
FIG. 3 shows one embodiment of an oligonucleotide array arranged according to the instant disclosure.

Proposed herein is an array of primers that segregated by the base to be incorporated in the extension reaction. As shown in FIG. 3, the entire array has four blocks, one for each of the incorporated bases, A, C, G, and T in the order in which the bases appear in the target gene.

Block A has sequentially addressed primers that are terminated with A, block C has sequentially addressed primers terminated with C. It is the same with block G and T. Therefore one can assemble the gene by base picking from the four blocks. If a mutation (or SNP) in a gene exists, it is revealed as a missing or mixed color spot in one block and confirmed as a missing or mixed color spot in the complementary base-pair block. This new format for arrayed primer extension would simplify the software requirement for de-convolution data analysis and visual recognition.

A particularly preferred method for anchoring oligonucleotides to the substrate is taught in U.S. application Ser. No. 09/388,702 filed on Sep. 2, 1999, entitled "Method for Anchoring Oligonucleotides to a Substrate," the entire disclosure of which is incorporated herein by reference. The substrate may be selected from a variety of materials, including glass, inorganic or organic polymer, and metal. Preferably, the substrate is glass. Although any type of glass may be used as a substrate, the preferred substrate is borosilicate glass. The substrate may take various physical forms, such as (but not limited to) slides or beads.

The surface of the substrate is modified to facilitate attachment of the oligonucleotide to the surface. The oligonucleotide is generally modified with a nucleophile, such as aminoalkyl, sulfhydryl and thiophosphate groups. The surface of the solid support is modified with a corresponding reactive group, such as substituted benzenesulfonate, methanesulfonate, and trifluoromethanesulfonate as leaving groups for the nucleophile on the primer. The reactive groups on the solid support can also be maleimide, vinylsulfonate and acrylate as electrophilic C=C double bonds for a nucleophile, and disulfide modification for disulfide exchange. The oligonucleotide can also be modified with biotin and the surface of the substrate coated with streptavidin or avidin. Preferred reactive groups for the oligonucleotide include thiophosphate, aminoalkyl and sulfhydryl. Most preferably, the reactive groups are thiophosphate.

Figure 5A:
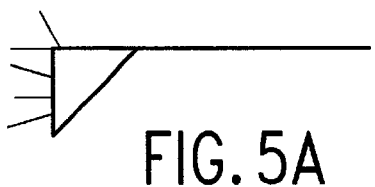
FIG. 5a shows one embodiment of the oligonucleotide primer as a tail structure having 5 groups capable of reacting with the surface of the substrate.
Figure 5B:
FIG. 5b shows one embodiment of the oligonucleotide primer having a closed loop structure.
Figure 5C:
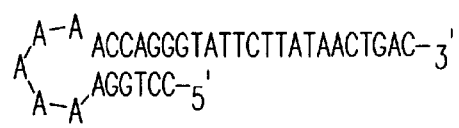
FIG. 5c shows one embodiment of the oligonucleotide primer as a hairpin molecule containing six nucleosides connected by thiophosphates in the loop and having a single-stranded 3' end and a 5' end in the double-stranded stem.
Figure 5D:
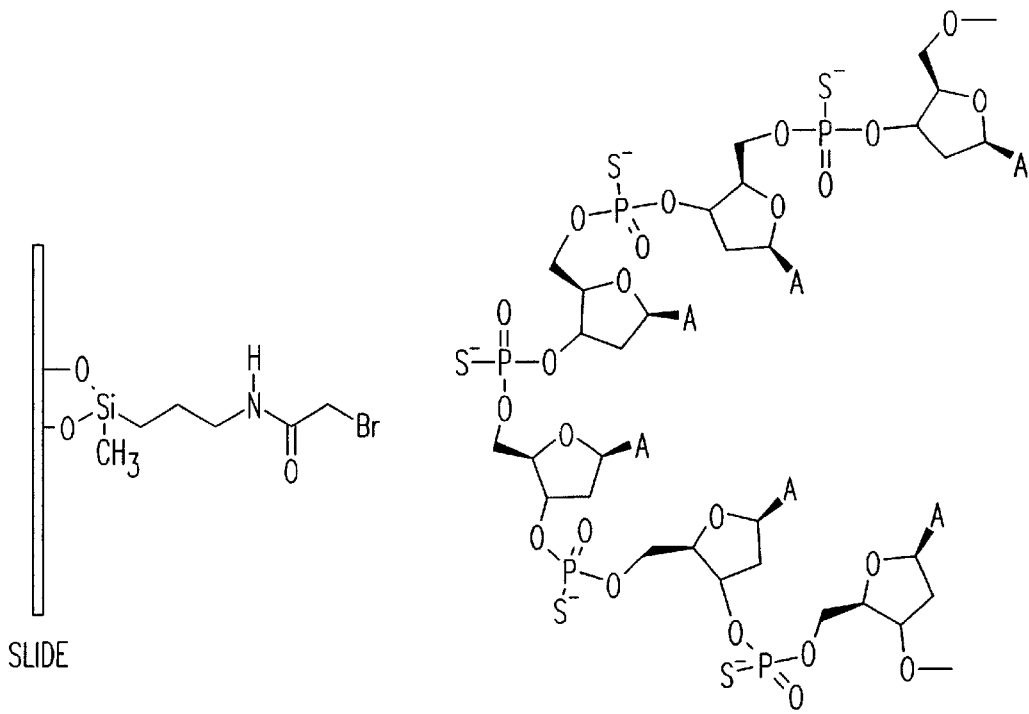
FIG. 5d shows a detailed view of the oligonucleotide primer depicted in FIG. 5c.

Multiple reactive groups on the oligonucleotide have been found to enhance reaction efficiency. Preferably, the subject oligonucleotides contain multiple groups in a single molecule capable of reacting with the surface of the substrate. In general, the oligonucleotide can contain any number of reactive groups. Preferably, the oligonucleotide contains from one to five reactive groups (see FIG. 5a which shows 5 reactive groups). The reactive groups may be arranged within one nucleoside of one another, or spaced throughout the oligonucleotide. Preferably, the reactive groups are arranged within two to six nucleosides of one another to create a hairpin structure in the oligonucleotide. The reactive groups may be the same or different. Although the subject oligonucleotides are not limited to those oligonucleotides having hairpin configurations; oligonucleotides having hair pin configurations such as those depicted in FIGS. 5c and 5d are preferred. Alternatively, the subject oligonucleotide may form a closed loop structure as shown in FIG. 5b.

Figure 4:
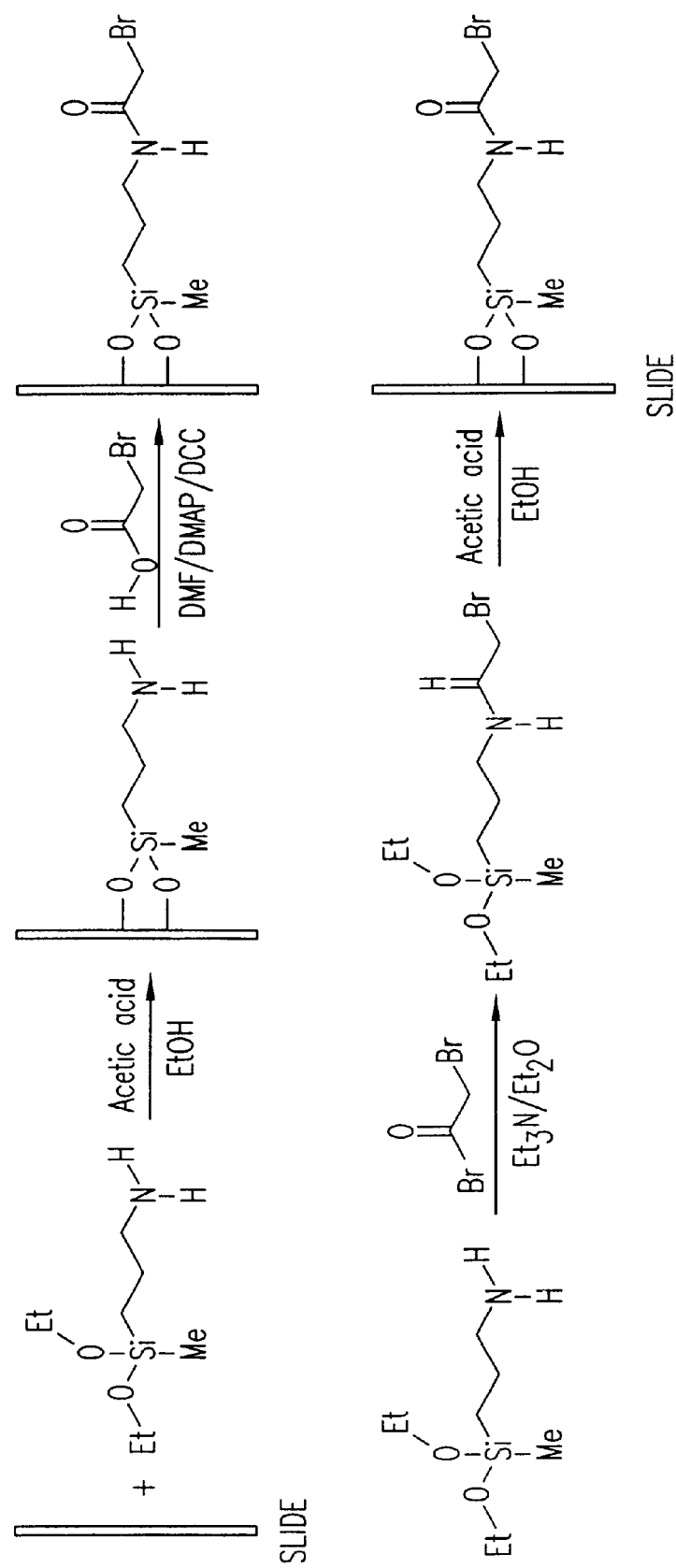
FIG. 4 shows one possible reaction scheme for preparing a bromoacetamide derivatized silane glass surface.

In a preferred embodiment, the glass substrate contains a bromoacetamide derivatized silane glass surface. FIG. 4 depicts one possible reaction scheme for preparing a bromoacetamide derivatized silane glass surface. The reactive slides can be prepared by starting from either regular glass slides or amine coated slides (commercially available from Amersham Pharmacia Biotech Inc and Corning Inc). The two-phase reaction is very efficient.

One preferred embodiment of the oligonucleotide is shown in FIG. 5c, and in greater detail in FIG. 5d. In FIGS. 5c and 5d, the oligonucleotide primer is a hairpin molecule containing six nucleosides in the loop. The nucleosides in the loop are connected by thiophosphates. The hairpin has a single-stranded 3' end and a 5' end in the double-stranded stem. The single-stranded tail is equivalent to a single-stranded oligonucleotide. This approach allows fast and efficient attachment by maintaining relatively low concentrations of oligonucleotide primers and high concentrations of reactive groups. Attachment of the primer to the bromoacetamide derivatized silane glass surface is shown in FIG. 6.

Because the oligonucleotide can attach to the substrate at any one of the reactive sites in the loop, the reaction probability (reaction rate and efficiency) increases with the number of reactive sites contained in the loop. In addition, as the anchorage of the oligonucleotide is in the backbone, both 5' and 3' ends are free for modifications with reporter groups. This is more versatile than when the anchors are at either 5' or 3' end. While a reaction occurs at one end, the other end is available for further labeling. Moreover, the hairpin structure has a stem-loop moiety, which adds extra parameters to space the oligonucleotides from each other and control the density and desired upward conformation of the single-stranded moiety for primer extension as well as ligation.

Figure 6:
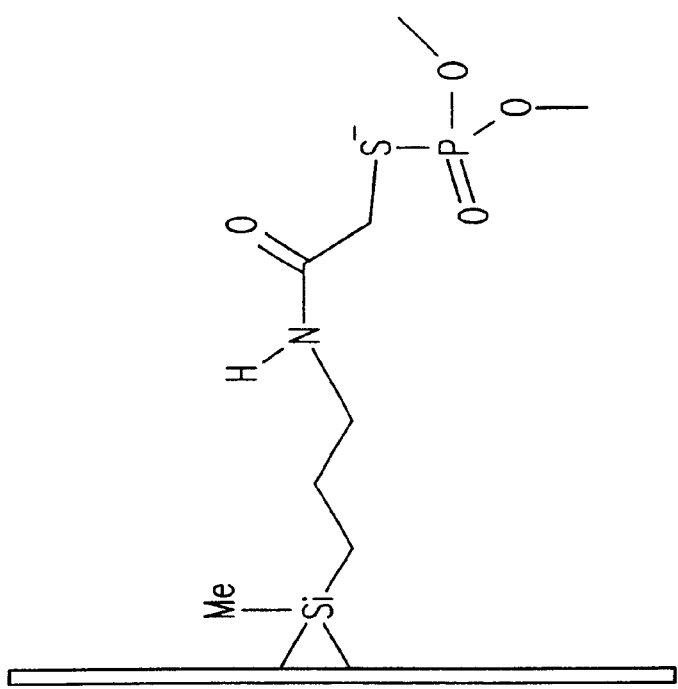
FIG. 6 shows the attachment reaction between the oligonucleotide primer depicted in FIG. 5 with the bromoacetamide derivatized silane glass surface shown in FIG. 4.
Figure 6:
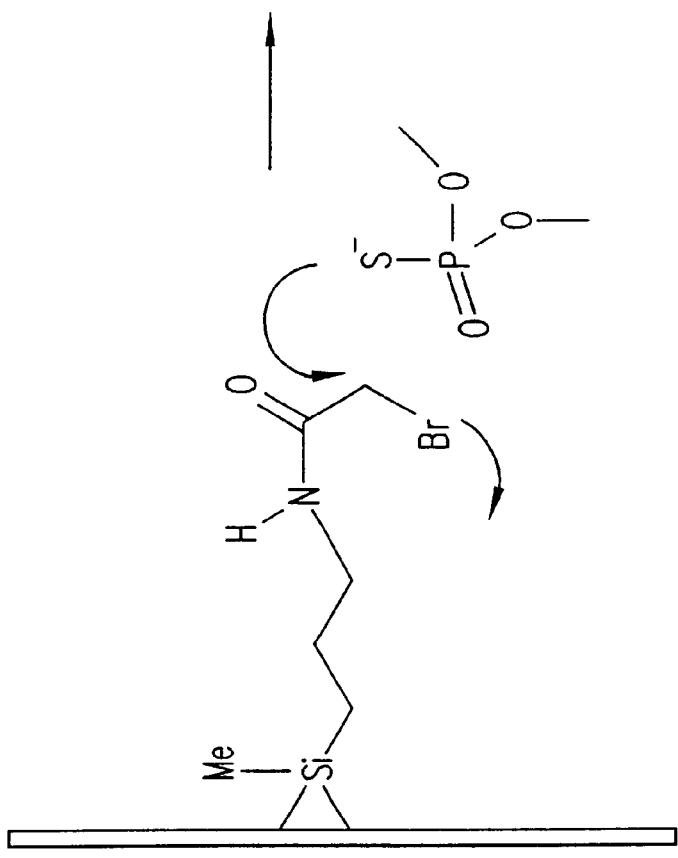
Figure 7:
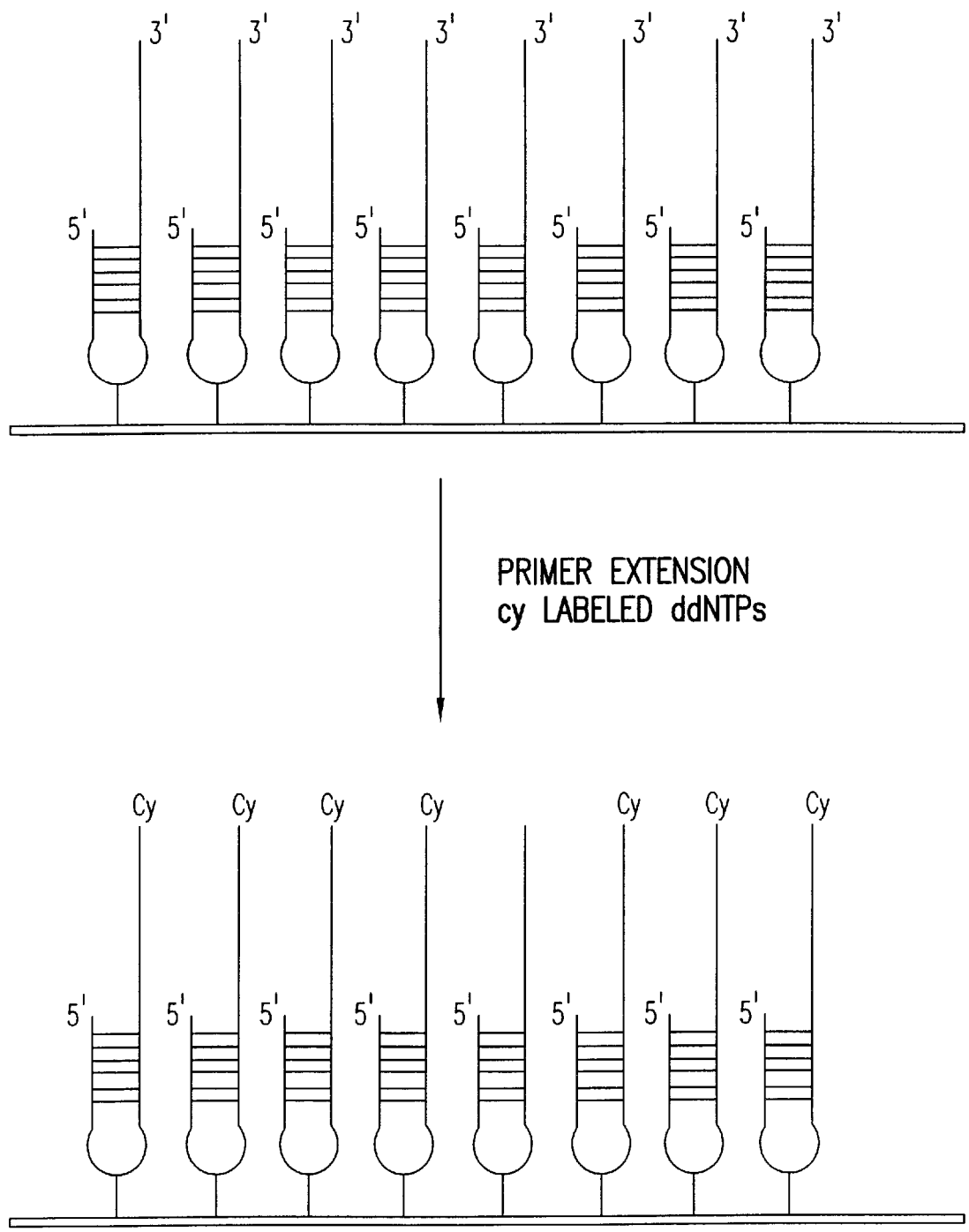
FIG. 7 shows one embodiment of an arrayed primer extension reaction involving certain oligonucleotide primers described herein.
Figure 8:
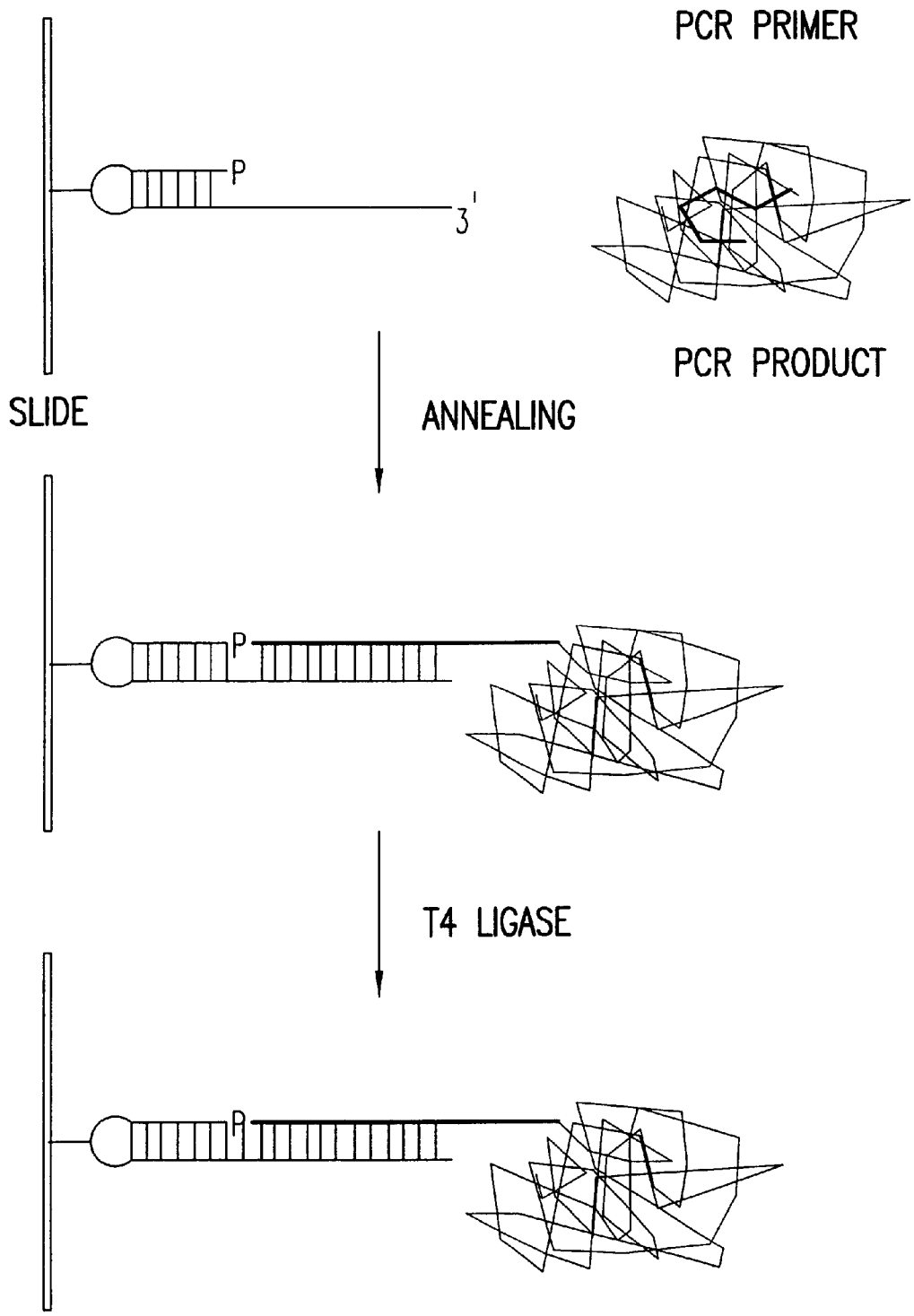
FIG. 8 shows one embodiment of a ligation reaction involving certain oligonucleotide primers described herein.

This attachment scheme offers significant advantages for immobilization of cDNA or any PCR product to microchips by hybridization and ligation (see FIGS. 6 and 7). For example, if then 5' end of the hairpin is phosphorylated chemically during synthesis and the 3' single-stranded tail has a sequence which is complementary to a PCR primer sequence, the PCR product could hybridize with the single-stranded tail and be linked covalently by enzymatic or chemical ligation. Many of the current approaches for covalently attaching a PCR product to a surface focus mainly on modifying PCR primers. One disadvantage of this approach is that the reactive position may be buried in the self-folded macromolecule. The approach of hybridization followed by ligation may have a higher reaction probability than the simple interaction of reactive groups, since such bimolecular reaction depends on more factors than the sole collision probability of two substrates. The instant method and oligonucleotides are not limited to the hybridization of nucleic acids. For example, the oligonucleotide primer may also contain a nucleotide sequence corresponding to a protein binding site and would be useful, for example, in protein assays.

The instant attachment method has the potential to immobilize oligonucleotides and DNAs by a covalent bond to a silica based glass surface with improved control of reaction efficiency, molecular density and conformation, and enzyme compatibility. Given the versatility of the instant oligonucleotides, it is possible that uses may be found with substrates other than those mentioned.

The instantly configured arrays may be used to detect mutations in sample nucleic acid sequences such as mRNA or DNA.

Terminators which are useful in the practice of the instant method may be selected from the group consisting of deoxynucleoside triphosphates and dideoxynucleoside triphosphates. Naturally occurring terminators, such as ddNTPs, may be used; however, synthetically-modified terminators, such as those containing a further methyl group blocking the 3' hydroxyl may also be used. The terminators useful in the practice of the instant method may be labeled in a variety of ways. For example, the labeled terminators may be labeled with a fluorescent dye, a chemiluminescent reagent, or a radioactive label. The terminators may also be labeled with a redox tag. For example, an organometallic tag, such as ferrocene, may be attached to the terminator and the change in electric potential at a particular spot on the microarray may be measured using a microelectrode. The labeled terminators may also be labeled with an electrically conductive tag and the change in conductivity at a particular spot on the microarray may be measured using a microelectrode.

Figure 1:
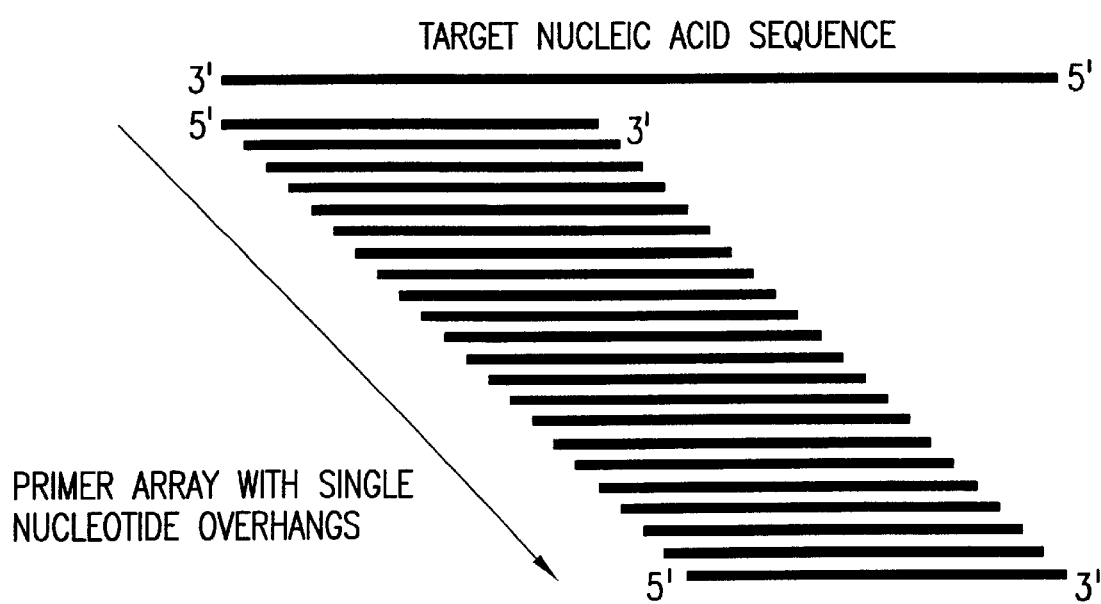
FIG. 1 shows a conventionally arranged oligonucleotide array.
Figure 2:
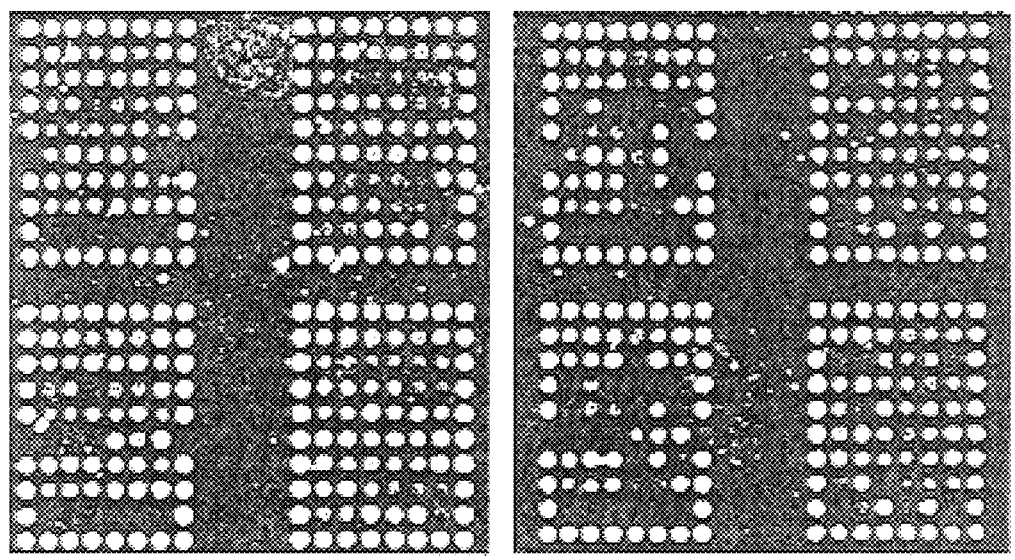
FIG. 2 shows a fluorescent image of a conventional oligonucleotide array which has been hybridized with a sample nucleic acid and subjected to a primer extension reaction. The four terminators are labeled with four fluorescent dyes. Each terminator that has been incorporated onto the oligonucleotide primer may be identified on the image by color. The image of the dye terminator labeled spots was obtained using an Avalanche microscanner (Molecular Dynamics, Sunnyvale, Calif.).

Variations of the instant method may be used with conventionally configured oligonucleotide arrays as well, i.e., those in which the oligonucleotides are laid on a chip sequentially from one end (3' or 5') to the other end (5' or 3') of the target, and one base difference is added as the oligonucleotides are arranged from one end of the chip to the other end (e.g., the oligonucleotide array configuration depicted in FIG. 1). Because the target nucleic acid sequence is already know, we are able to predict the identity of the base which is expected to be added to a primer that is located at a particular coordinate on an oligonucleotide array. This information may be entered into a computer program. After hybridization and subsequent primer extension, it is possible to identify the base actually added to the primer located at the particular coordinate on the oligonucleotide array. This information may also be entered into the computer program. If we compare the base actually added to the primer at the particular coordinate with the base that was expected to be added to the primer at the particular coordinate (e.g., using the computer program), we will be able to detect mutations in a target nucleic acid sequence by identifying those instances where the base actually added to the primer is not the same as the base which was expected to be added to the primer at that particular coordinate on the array.

The instantly disclosed method for detecting mutations using arrayed primer extension has simplicity of experiment, software development and data analysis. This method allows the researcher to immediately identify mutations using the naked eye. It can eliminate de-convolution errors by calibrating multiple standards and serve to reduce overall error rate for application in diagnostics. This conception could also be used for software design even for an array prepared as the conventional format. The following examples are for illustration purposes only and should not be used in any way to limit the appended claims.

EXAMPLES

Slide Preparation

Pre-washed glass slides (25×75 mm microscope slides from VWR Scientific Products West Chester, Pa.) were immersed for 3 minutes in 95% ethanol (350 mL) containing approximately 2% (wt/vol) 3-aminopropylmethylethoxysilane, pH 5.0, washed with ethanol, and cured in an oven at 75° C. for 4 hours. After curing, the glass slides were placed on a glass rack and immersed in 160 mL of N,N-dimethylformamide (DMF) containing bromoacetic acid (0.45 g, 3.3 mmol), 4-(dimethylamino)-pyridine (DMAP) (0.04 g, 0.3 mmol), and 1,3-dicyclohexylcarbodiimide (DCC) (0.66 g, 3.2 mmol). The reaction was stirred in the dark for 2 hours. The slides were then washed with ethanol and air-dried.

Array Preparation

Four primers were specifically designed for sense strand of human p53 gene exon 6. The primers were purchased from Sigma-Genosys (The Woodland, Tex.). Their sequences are as below:

(Primer 1) aaaTGGCCCCTCCTCAGCATCTTATCCG (SEQ ID NO: 1)

(Primer 2) aaaTCACTGATTGCTCTTAGGTCTGGCC (SEQ ID NO: 2)

(Primer 3) aaaTTCCTCACTGATTGCTCTTAGGTCT (SEQ ID NO: 3)

(Primer 4) aaaACTGATTGCTCTTAGGTCTGGCCCC (SEQ ID NO: 4)

Three adjacent thiophosphates are located to the right of lower case a's in each primer sequence. The hairpin oligonucleotide was dissolved and stored in 1×TE (10 mM Tris.HCl, 1 mM EDTA, pH 7.0). The concentration of oligonucleotide was calculated based on spectrophotometric measurement. The primers (50 $\mu$M) were spotted on a bromoacetamide silane coated glass surface using a Molecular Dynamics Gen III spotter (Molecular Dynamics, Sunnyvale, Calif.). The volume of the spots was 0.7 nL and the size was 130 $\mu$m in diameter. The primers were spotted in four blocks on a chip. Primer (1) was spotted in an 8×8 spot block, which can be extended by a DNA polymerase with dye labeled ddATP. Primer (2) was spotted in another block, which can be extended by a DNA polymerase with dye labeled ddCTP. Similarly, primers (3) and (4) were spotted in a third and fourth block respectively, which can be extended by a DNA polymerase with dye labeled ddGTP and ddTTP respectively.

Primer Extension

The slide with primers was placed on a hot plate heated to 48° C. Primer extension was carried out in 45 $\mu$L of Thermo Sequenase buffer (25 mM TAPS buffer, pH9.3, 50 mM KCl, 2 mM MgCl$_2$, 1 mM 2-mercaptoethanol) with 0.5 $\mu$M of dye terminators Cy5-ddATP, Cy3-ddCTP, Cy5.5-ddGTP, and Cy3.5-ddTTP, and Thermo Sequenase DNA polymerase (4 unit). The templates were PCR products of human p53 gene exon 6. The reaction mixture was washed away with boiling water after being incubated for 10 minutes. The image of the dye terminator labeled spots was obtained using an Avalanche microscanner (Molecular Dynamics, Sunnyvale, Calif.) and is shown in FIG. 3 above.

Although various embodiments of the instant invention are described in detail above, the instant invention is not limited to such specific examples. Various modifications will be readily apparent to one of ordinary skill in the art and fall within the spirit and scope of the following appended claims.

What is claimed is:

1. A method for detecting a mutation in a target nucleic acid sequence that comprises:
   A. attaching oligonucleotide primers to a substrate, wherein the oligonucleotide primers have a sequence that is complementary to the target nucleic acid sequence, and wherein the oligonucleotide primers are grouped according to the identity of the first base which would be expected to be added to the primer through the process of primer extension;
   B. hybridizing to the oligonucleotide primers a sample nucleic acid sequence which possibly contains a mutation;
   C. extending each oligonucleotide primer by one base using a reaction mixture comprising labeled terminators and enzyme; and
   D. detecting a mutation in the sample nucleic acid sequence by detecting the presence of a labeled terminator which does not correspond to the identity of the base expected to be added to the primer through the process of primer extension.

2. The method of claim 1, wherein the sample nucleic acid sequence is mRNA.

3. The method of claim 1, wherein the sample nucleic acid sequence is DNA.

4. The method of claim 1, wherein the labeled terminators are selected from the group consisting of deoxynucleoside triphosphates and dideoxynucleoside triphosphates.

5. The method of claim 4, wherein the labeled terminators are synthetically modified.

6. The method of claim 1, wherein the labeled terminators are labeled with a fluorescent dye.

7. The method of claim 1, wherein the labeled terminators are labeled with a chemiluminescent reagent.

8. The method of claim 1, wherein the labeled terminators are labeled with a radioactive label.

9. The method of claim 1, wherein the labeled terminators are labeled with a redox tag.

10. The method of claim 1, wherein the labeled terminators are labeled with an electrically conductive tag.

11. A nucleic acid array comprising a substrate containing oligonucleotide primers having a sequence complementary to a target nucleic acid sequence, wherein the oligonucleotide primers are grouped according to the identity of the first base which would be expected to be added to the primer through the process of primer extension after hybridizing with a sample nucleic acid sequence.

12. A kit for detecting genetic mutations comprising the nucleic acid array according to claim 11.

* * * * *